(12) United States Patent
Altmayer

(10) Patent No.: US 6,210,465 B1
(45) Date of Patent: Apr. 3, 2001

(54) METHOD FOR IDENTIFICATION OF COMPONENTS WITHIN A KNOWN SAMPLE

(75) Inventor: Lee H. Altmayer, Wilmington, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/270,854

(22) Filed: Mar. 17, 1999

(51) Int. Cl.⁷ .................................................. B01D 15/08
(52) U.S. Cl. ........................... 95/82; 73/23.22; 73/23.36; 96/103
(58) Field of Search ................... 95/82–89; 96/101–107; 73/23.22, 23.23, 23.35, 23.36

(56) References Cited

U.S. PATENT DOCUMENTS

| | | | |
|---|---|---|---|
| 4,719,017 | * | 1/1988 | Uchino et al. ........................ 95/82 X |
| 5,108,466 | * | 4/1992 | Klein et al. .......................... 95/82 X |
| 5,405,432 | * | 4/1995 | Snyder et al. ........................ 95/87 X |
| 5,436,166 | * | 7/1995 | Ito et al. .............................. 95/82 X |
| 5,545,252 | * | 8/1996 | Hinshaw et al. ..................... 95/82 X |
| 5,567,227 | * | 10/1996 | Henderson ........................... 95/82 X |
| 5,642,278 | * | 6/1997 | Wang et al. ......................... 96/102 X |
| 5,670,379 | * | 9/1997 | Ito et al. .............................. 95/82 X |
| 5,711,786 | * | 1/1998 | Hinshaw ................................. 95/82 |
| 5,892,458 | * | 4/1999 | Anderer et al. ...................... 95/82 X |
| 5,939,612 | * | 8/1999 | Wylie et al. ......................... 95/82 X |
| 5,958,246 | * | 8/1999 | Tipler et al. ......................... 95/82 X |

* cited by examiner

Primary Examiner—Robert H. Spitzer

(57) ABSTRACT

A method for identifying components within a known type of sample through pattern recognition between an array of recognition coefficients generated from the attributes and stable relationships of a plurality of peaks within a chromatogram of a sample to be analyzed and a similar array of recognition coefficients generated from the attributes and stable relationships of a plurality of peaks from a set of one or more historical chromatograms of the known type of sample. The group of attributes include, but are not limited to: retention time, peak shape including symmetry, width and duration, peak size including area and height, and algorithmic measures of peak type.

23 Claims, 14 Drawing Sheets

```
ALL pks:  10

RT                    AREA                    SYMMETRY               Peak TYPE              Peak WIDTH
    o[1,1] = 1.579,     o[1,2] = 1.,     o[1,3] = 1.,     o[1,4] = 800.,   o[1,5] = .
1,  opn[1,1] = 1.51,    opn[1,2] = 1.,   opn[1,3] = .83,  opn[1,4] = 800., opn[1,5] = .008
1,  opm[1,1] = 1.62,    opm[1,2] = 1.,   opm[1,3] = 1.08, opm[1,4] = 810., opm[1,5] = .012 o[2,1] = 2.35,      o[2,2] = 1.,     o[2,3] = 1.,     o[2,4] = 800.,   o[2,5] = .
2,  opn[2,1] = 2.31,    opn[2,2] = 1.,   opn[2,3] = .9,   opn[2,4] = 800., opn[2,5] = .011
2,  opm[2,1] = 2.41,    opm[2,2] = 1.,   opm[2,3] = 1.7,  opm[2,4] = 904., opm[2,5] = .013 o[3,1] = 3.402,     o[3,2] = 1.,     o[3,3] = 1.,     o[3,4] = 800.,   o[3,5] = .
3,  opn[3,1] = 3.35,    opn[3,2] = 1.,   opn[3,3] = .91,  opn[3,4] = 800., opn[3,5] = .013
3,  opm[3,1] = 3.45,    opm[3,2] = 1.,   opm[3,3] = 2.01, opm[3,4] = 804., opm[3,5] = .015 o[4,1] = 3.815,     o[4,2] = 1.,     o[4,3] = 1.,     o[4,4] = 800.,   o[4,5] = .
4,  opn[4,1] = 3.79,    opn[4,2] = 1.,   opn[4,3] = .91,  opn[4,4] = 800., opn[4,5] = .013
4,  opm[4,1] = 3.85,    opm[4,2] = 1.,   opm[4,3] = 1.91, opm[4,4] = 811., opm[4,5] = .015 o[5,1] = 3.962,     o[5,2] = 1.,     o[5,3] = 1.,     o[5,4] = 800.,   o[5,5] = .
5,  opn[5,1] = 3.91,    opn[5,2] = 1.,   opn[5,3] = .91,  opn[5,4] = 800., opn[5,5] = .014
5,  opm[5,1] = 3.99,    opm[5,2] = 1.,   opm[5,3] = 1.61, opm[5,4] = 812., opm[5,5] = .016 o[6,1] = 6.561,     o[6,2] = 1.,     o[6,3] = 1.,     o[6,4] = 800.,   o[6,5] = .
6,  opn[6,1] = 6.51,    opn[6,2] = 1.,   opn[6,3] = .85,  opn[6,4] = 800., opn[6,5] = .015
6,  opm[6,1] = 6.57,    opm[6,2] = 1.,   opm[6,3] = 1.61, opm[6,4] = 811., opm[6,5] = .018 o[7,1] = 7.466,     o[7,2] = 1.,     o[7,3] = 1.,     o[7,4] = 800.,   o[7,5] = .
7,  opn[7,1] = 7.41,    opn[7,2] = 1.,   opn[7,3] = .85,  opn[7,4] = 800., opn[7,5] = .016
7,  opm[7,1] = 7.51,    opm[7,2] = 1.,   opm[7,3] = 4.01, opm[7,4] = 805., opm[7,5] = .021 o[8,1] = 8.303,     o[8,2] = 1.,     o[8,3] = 1.,     o[8,4] = 800.,   o[8,5] = .
8,  opn[8,1] = 8.28,    opn[8,2] = 1.,   opn[8,3] = .91,  opn[8,4] = 800., opn[8,5] = .016
8,  opm[8,1] = 8.42,    opm[8,2] = 1.,   opm[8,3] = 20.1, opm[8,4] = 999., opm[8,5] = .05 o[9,1] = 9.795,     o[9,2] = 1.,     o[9,3] = 1.,     o[9,4] = 800.,   o[9,5] = .
9,  opn[9,1] = 9.75,    opn[9,2] = 1.,   opn[9,3] = .81,  opn[9,4] = 800., opn[9,5] = .016
9,  opm[9,1] = 9.85,    opm[9,2] = 1.,   opm[9,3] = 1.51, opm[9,4] = 811., opm[9,5] = .021 o[10,1] = 12.504,  o[10,2] = 1.,    o[10,3] = 1.,    o[10,4] = 800.,  o[10,5] = .
10,  opn[10,1] = 12.48, opn[10,2] = 1.,  opn[10,3] = .51, opn[10,4] = 800.,opn[10,5] = 0.23
10,  opm[10,1] = 12.52, opm[10,2] = 1.,  opm[10,3] = 2.01,opm[10,4] = 811.,opm[10,5] = .032
```

MEAN → 
MINIMUM → 
MAXIMUM →

FIG. 4A $$\left\{\begin{array}{l}\left\{\begin{array}{l}\text{PEAK} = \qquad 8 \\ \text{RT\quad AREA\quad SYM\quad TYPE\quad WIDTH\quad HEIGHT\quad BL\quad DUR} \\ 8.305\,,\,375.43\,,\,1.0506\,,\,800\,,\,.0177\,,\,336.984\,,\,12.508\,,\,.07833 \\ 8.306\,,\,383.49\,,\,1.1589\,,\,800\,,\,.017\,,\,358.448\,,\,12.863\,,\,.08917 \\ 8.306\,,\,381.8\,,\,1.1043\,,\,800\,,\,.0175\,,\,341.709\,,\,13.24\,,\,.07167 \\ 8.304\,,\,214.05\,,\,.964\,,\,800\,,\,.0164\,,\,201.131\,,\,13.322\,,\,.075 \\ 8.339\,,\,7995.56\,,\,4.1447\,,\,806\,,\,.023\,,\,4598.785\,,\,13.21\,,\,.11282 \\ 8.342\,,\,8003.48\,,\,4.8806\,,\,806\,,\,.022\,,\,4729.644\,,\,13.542\,,\,.1138 \\ 8.337\,,\,7099.45\,,\,3.9827\,,\,804\,,\,.0219\,,\,4320.77\,,\,13.453\,,\,.11404 \\ 8.347\,,\,9970.56\,,\,4.7889\,,\,806\,,\,.0242\,,\,5297.951\,,\,13.236\,,\,.11446 \\ 8.347\,,\,10099.27\,,\,4.3573\,,\,806\,,\,.0263\,,\,5289.608\,,\,13.124\,,\,.11345 \\ 8.347\,,\,10241.67\,,\,4.7692\,,\,806\,,\,.0251\,,\,5401.202\,,\,13.076\,,\,.11286 \\ \ldots \\ \ldots\ldots\,\text{MANY LINES DELETED}\,\ldots \\ \ldots \\ 8.358\,,\,14909.16\,,\,6.676\,,\,806\,,\,.0288\,,\,6561.527\,,\,13.084\,,\,.11573 \\ 8.358\,,\,15038.45\,,\,6.3065\,,\,806\,,\,.0283\,,\,6743.925\,,\,13.106\,,\,.11588 \\ 8.414\,,\,56997.55\,,\,13.0446\,,\,904\,,\,.0488\,,\,14443.876\,,\,13.211\,,\,.29268 \\ 8.393\,,\,38480.27\,,\,11.0279\,,\,904\,,\,.0419\,,\,11610.245\,,\,13.215\,,\,.19916 \\ 8.394\,,\,38554.65\,,\,10.292\,,\,904\,,\,.04\,,\,12007.087\,,\,13.236\,,\,.19687 \\ 8.393\,,\,38527.81\,,\,10.4912\,,\,904\,,\,.0413\,,\,11431.303\,,\,13.188\,,\,.19875 \\ 8.382\,,\,28926.89\,,\,11.6228\,,\,904\,,\,.0357\,,\,10015.506\,,\,13.099\,,\,.18778 \\ 8.338\,,\,7933.16\,,\,4.1051\,,\,806\,,\,.023\,,\,4521.036\,,\,13.121\,,\,.10586\end{array}\right\}\end{array}\right\}\text{HISTORICAL DATA}$$

STATISTICAL PROPERTIES OVER FULL RANGE:
- 68., 68., 68., 68, 68., 68., 68., 68.,
- 8.3, 128.21, .964, 800, .0159, 114.466, 12.13, .0675 ← MINIMUM
- 8.416, 56997.55, 13.0446, 910, .0493, 14707.693, 13.596, .465 ← MAXIMUM
- 8.341, 13955.02, 4.8749, 833, .026, 4985.53, 13.125, .14217, ← MEAN
- .037, 17189.68, 3.8991, 46, .0103, 4645.949, .247, .07857 ← STANDARD DEVIATION (2ND MOMENT)

MOMENTS: SKEW & KURTOSIS ← MEASURES OF DISPERSION

- .585, 1.23, .704, 1, .9496, .625, -1.82, 1.9874 ← (3RD MOMENT)
- 1.985, 3.26, 2.1366, 2, 2.5658, 2.084, 8.344, 7.39719 ← (4TH MOMENT)

GOODNESS OF FIT FUNCTIONS:

$$\text{MEDIAN AREA} = \underset{c_1}{-5465.5} + \underset{c_2}{213.26 \times RT} + \underset{c_3}{1.410 \times RT^2} \qquad R^2 = .9981$$

$$\text{MEDIAN AREA} = \underset{c_4}{-2334.3} + \underset{c_5}{2.6767 \times \text{wid}} + \underset{c_6}{0.000080 \times \text{wid}^2} \qquad R^2 = .9947$$

$$\text{MEDIAN AREA} = \underset{c_7}{-4069.1} + \underset{c_8}{1.3166 \times \text{sym}} + \underset{c_9}{0.000037 \times \text{sym}^2} \qquad R^2 = .9652$$

($R^2$ IS A KNOWN STATISTICAL FUNCTION REPRESENTING GOODNESS OF FIT)

FIG. 4B

METHOD STEPS REQUIRED TO GENERATE THE DATA DISPLAYED IN FIGURE 4B

1) COMPILE HISTORICAL DATA FOR PEAK, I, WITH ATTRIBUTE, J, FROM CHROMATOGRAM K INTO AN ARRAY P(I,J,K) FOR I=8, PEAK C24 FOR ALL 8 ATTRIBUTES [J=1 TO 8] FOR RUNS FROM K=1 TO 68

2) PRINT CONTENTS OF P(8,J,K)  (THIS SHOWS ALL 8 ATTRIBUTES FOR THE 68 RUNS AT TOP OF FIGURE 4B)

3) COMPUTE THE STATISTICAL PROPERTIES OF EACH ATTRIBUTE (J) OVER ALL K RUNS [K=1 TO 68] INCLUDING, MINIMUM, MAXIMUM $$\text{MEAN} = \frac{\sum_{K=1}^{N} X(K)}{N}$$

$$\text{STANDARD DEVIATION} = \sqrt{\frac{\sum_{K=1}^{N}(X(K)-\text{MEAN})^2}{N-1}}$$

$$\text{SKEW} = \frac{\sqrt{N}\sum_{K=1}^{N}(X(K)-\text{MEAN}))^3}{\sum_{K=1}^{N}((X(K)-\text{MEAN})^2)^{3/2}}$$

4) USING STANDARD LEAST SQUARES REGRESSION ANALYSIS FIT SELECTED ATTRIBUTES WITH SMALLER VARIATION AS A FUNCTION OF ATTRIBUTES WITH THE GREATEST VARIATION. DISPLAY REGRESSION COEFFICIENTS AND GOODNESS OF FIT INDICATOR FOR LINEAR AND NON-LINEAR MODELS.

FIG. 4C

| PEAK | | | | | |
|------|---|---|---|---|---|
| 211 { | 1, | pm[1,1] = 1.579, | pm[1,2] = 1., | pm[1,3] = 1., | pm[1,4] = 800., | pm[1,5] = . |
| | 1, | pm[1,1] = 1.579, | pm[1,2] = 1., | pm[1,3] = 1., | pm[1,4] = 800., | pm[1,5] = . |
| | 1, | pmn[1,1] = 1.51, | pmn[1,2] = 1., | pmn[1,3] = 1.1, | pmn[1,4] = 800., | pmn[1,5] = .008 |
| | 1, | pmx[1,1] = 1.62, | pmx[1,2] = 1., | pmx[1,3] = 1.08, | pmx[1,4] = 810., | pmx[1,5] = .012 |
| 213 { | 2, | pm[2,1] = 3.402, | pm[2,2] = 1., | pm[2,3] = 1., | pm[2,4] = 800., | pm[2,5] = . |
| | 2, | pm[2,1] = 3.402, | pm[2,2] = 1., | pm[2,3] = 1., | pm[2,4] = 800., | pm[2,5] = . |
| | 2, | pmn[2,1] = 3.35, | pmn[2,2] = 1.51, | pmn[2,3] = .91, | pmn[2,4] = 800., | pmn[2,5] = .013 |
| | 2, | pmx[2,1] = 3.45, | pmx[2,2] = 2000., | pmx[2,3] = 2.01, | pmx[2,4] = 804., | pmx[2,5] = .015 |
| 214 { | 3, | pm[3,1] = 3.815, | pm[3,2] = 1., | pm[3,3] = 1., | pm[3,4] = 800., | pm[3,5] = . |
| | 3, | pm[3,1] = 3.015, | pm[3,2] = 1., | pm[3,3] = 1., | pm[3,4] = 800., | pm[3,5] = . |
| | 3, | pmn[3,1] = 3.79, | pmn[3,2] = 1.51, | pmn[3,3] = .91, | pmn[3,4] = 800., | pmn[3,5] = .013 |
| | 3, | pmx[3,1] = 3.85, | pmx[3,2] = 2000., | pmx[3,3] = 1.91, | pmx[3,4] = 811., | pmx[3,5] = .015 |
| 215 { | 4, | pm[4,1] = 3.962, | pm[4,2] = 1., | pm[4,3] = 1., | pm[4,4] = 800., | pm[4,5] = . |
| | 4, | pm[4,1] = 3.962, | pm[4,2] = 1., | pm[4,3] = 1., | pm[4,4] = 800., | pm[4,5] = . |
| | 4, | pmn[4,1] = 3.91, | pmn[4,2] = 1.51, | pmn[4,3] = .91, | pmn[4,4] = 800., | pmn[4,5] = .014 |
| | 4, | pmx[4,1] = 3.99, | pmx[4,2] = 1000., | pmx[4,3] = 1.61, | pmx[4,4] = 812., | pmx[4,5] = .016 |
| 218 { | 5, | pm[5,1] = 8.303, | pm[5,2] = 1., | pm[5,3] = 1., | pm[5,4] = 800., | pm[5,5] = . |
| | 5, | pm[5,1] = 8.303, | pm[5,2] = 1., | pm[5,3] = 1., | pm[5,4] = 800., | pm[5,5] = . |
| | 5, | pmn[5,1] = 8.28, | pmn[5,2] = 100.1, | pmn[5,3] = .91, | pmn[5,4] = 800., | pmn[5,5] = .016 |
| | 5, | pmx[5,1] = 8.42, | pmx[5,2] = 99999., | pmx[5,3] = 20.1, | pmx[5,4] = 999., | pmx[5,5] = .05 |
| 222 { | 6, | pm[6,1] = 12.504, | pm[6,2] = 1., | pm[6,3] = 1., | pm[6,4] = 800., | pm[6,5] = . |
| | 6, | pm[6,1] = 12.504, | pm[6,2] = 1., | pm[6,3] = 1., | pm[6,4] = 800., | pm[6,5] = . |
| | 6, | pmn[6,1] = 12.48, | pmn[6,2] = 1.1, | pmn[6,3] = .51, | pmn[6,4] = 800., | pmn[6,5] = .023 |
| | 6. | pmx[6,1] = 12.52, | pmx[6,2] = 999., | pmx[6,3] = 2.01, | pmx[6,4] = 811., | pmx[6,5] = .032 |

FIG. 5

|   | RT | TYPE | SYMMETRY | AREA | WIDTH | HEIGHT | BASELINE VALUE | DURATION |
|---|---|---|---|---|---|---|---|---|
| 1 | 01.577 | 800 | 0.958 | 0000000003.47 | 00.008 | 0000000006.67 | 000012.13 | 00.033 |
| 2 | 02.348 | 800 | 0.973 | 0000000010.58 | 00.011 | 0000000014.71 | 000012.14 | 00.068 |
| 3 | 03.402 | 801 | 1.009 | 0000000007.07 | 00.013 | 0000000008.19 | 000012.15 | 00.049 |
| 4 | 03.814 | 800 | 0.997 | 0000000007.27 | 00.013 | 0000000008.64 | 000012.18 | 00.078 |
| 5 | 03.962 | 800 | 1.011 | 0000000005.34 | 00.014 | 0000000005.93 | 000012.17 | 00.046 |
| 6 | 06.561 | 801 | 0.960 | 0000000003.71 | 00.016 | 0000000003.61 | 000012.27 | 00.049 |
| 7 | 07.467 | 801 | 0.993 | 0000000038.92 | 00.016 | 0000000036.67 | 000012.39 | 00.063 |
| 8 | 08.305 | 800 | 1.051 | 0000000375.43 | 00.018 | 0000000336.98 | 000012.51 | 00.078 |
| 9 | 08.498 | 804 | 0.839 | 0000000003.56 | 00.018 | 0000000003.06 | 000012.50 | 00.064 |
| 10 | 08.914 | 800 | 1.121 | 0000000001.25 | 00.019 | 0000000001.03 | 000012.57 | 00.058 |
| 11 | 09.799 | 801 | 1.026 | 0000000004.00 | 00.017 | 0000000003.60 | 000012.75 | 00.057 |
| 12 | 12.513 | 801 | 1.133 | 0000000004.14 | 00.026 | 0000000002.12 | 000014.95 | 00.096 |

FIG. 6

700 START

702 N=0          (RESET REQUIRED PEAK COUNTER N BACK TO 0)

703 N=N+1          (INCREMENT REQUIRED PEAK COUNTER BY 1)

704 IF N=NUMBER OF REQUIRED PEAKS+1, THEN GO TO 750
(THIS STEP REVIEWS ATTRIBUTES FOR REQUIRED PEAKS, FOR N=1 TO THE TOTAL NUMBER OF REQUIRED PEAKS, AND IF THE LAST REQUIRED PEAK IS FOUND, THEN EXIT)

710 SET C=0   (RESET PEAK COUNTER C TO FIRST PEAK)

715 C=C+1 (THIS STEP SETS UP A LOOP FOR REVIEWING THE ATTRIBUTES OF EACH PEAK TO ASCERTAIN WHETHER EACH PEAK PASSES ALL THE SCREENS AND IS IDENTIFIED AS A REQUIRED PEAK CANDIDATE)

720 IF RT OF PEAK C NOT WITHIN RANGE OF HISTORICAL DATA, GO TO 740

721 IF PEAK TYPE OF PEAK C NOT WITHIN RANGE OF HISTORICAL DATA, GO TO 740

722 IF SYMMETRY OF PEAK C NOT WITHIN RANGE OF HISTORICAL DATA, GO TO 740

723 IF AREA OF PEAK C NOT WITHIN RANGE OF HISTORICAL DATA, GO TO 740

724 IF WIDTH OF PEAK C NOT WITHIN RANGE OF HISTORICAL DATA, GO TO 740

725 IF HEIGHT OF PEAK C NOT WITHIN RANGE OF HISTORICAL DATA, GO TO 740

726 IF BASELINE VALUE OF PEAK C NOT WITHIN RANGE OF HISTORICAL DATA, GO TO 740

727 IF PEAK DURATION OF PEAK C NOT WITHIN RANGE OF HISTORICAL DATA, GO TO 740

730 MARK CURRENT PEAK AS A CANDIDATE

740 IF C=NUMBER OF PEAKS PRESENT, THEN GO TO 703    (THIS STEP CHECKS TO SEE IF THE LAST PEAK WAS TESTED FOR THE ATTRIBUTES OF REQUIRED PEAK N, IF SO, THEN GO ON TO NEXT REQUIRED PEAK)

745 GO TO 715     (TO CONTINUE TO TEST PEAKS THAT ARE PRESENT)

750 STOP

FIG. 7

| 800 | START |
| 810 | N=0 |
| 820 | N=N+1     (INCREMENT COUNTER FOR REQUIRED PEAKS) |
| 821 | C=0 |
| 822 | IF N=NUMBER OF REQUIRED PEAKS +1, THEN GO TO 880 |
| 823 | C=C+1 |
| 825 | IF AREA ATTRIBUTE OF PEAK C NOT WITHIN LIMITS FOR REQUIRED PEAK, THEN GO TO 823   (THIS PEAK IS NOT MATCHED) |
| 830 | IF AREA ATTRIBUTE OF PEAK C OUTSIDE NORMAL RANGE FOR REQUIRED PEAK, THEN GO TO 850 |
| 840 | USE DEFAULT SET OF ATTRIBUTES TO IDENTIFY REQUIRED PEAK GO TO 862 |
| 850 | COMPUTE NEW SET OF ATTRIBUTES FOR REQUIRED PEAK, BASED ON NON-LINEAR EQUATION WITH COEFFICIENTS |
| 862 | IF RT OF PEAK C NOT WITHIN RANGE OF ATTRIBUTES, GO TO 872 |
| 863 | IF PEAK TYPE OF PEAK C NOT WITHIN RANGE OF ATTRIBUTES, GO TO 872 |
| 864 | IF SYMMETRY OF PEAK C NOT WITHIN RANGE OF ATTRIBUTES, GO TO 872 |
| 865 | IF WIDTH OF PEAK C NOT WITHIN RANGE OF ATTRIBUTES, GO TO 872 |
| 866 | IF HEIGHT OF PEAK C NOT MITHIN RANGE OF ATTRIBUTES, GO TO 872 |
| 867 | IF BASELINE VALUE OF PEAK C NOT WITHIN RANGE OF ATTRIBUTES, GO TO 872 |
| 868 | IF DURATION OF PEAK C NOT WITHIN RANGE OF ATTRIBUTES, GO TO 872 |
| 870 | MARK CURRENT PEAK AS A PEAK CANDIDATE |
| 872 | IF C=NUMBER OF PEAKS PRESENT, THEN GO TO 820 |
| 874 | GO TO 823 |
| 880 | STOP |

FIG. 8

RETENTION TIME ERRORS COMPUTED FOR REQUIRED PEAKS ARE USED TO GENERATE A "SHIFT" VALUE.

901    RESET AVG_SHIFT TO 0

902    RESET MAXIMUM_SHIFT TO 0

903    RESET REQUIRED_PEAK_COUNT TO 0          ! END OF INITIALIZE

910    INCREMENT REQUIRED_PEAK_COUNT           ! LOOP FOR ALL REQUIRED PEAKS

911    IF REQUIRED_PEAK_COUNT > LAST_REQUIRED_PEAK
       THEN GO TO 1000

912    IF REQUIRED PEAK NOT FOUND,
       THEN GO TO 910

920    FOR EACH REQUIRED PEAK FOUND, COMPUTE
       ABSOLUTE VALUE AS PERCENTAGE SHIFT FOR THIS
       PEAK:

$$X = 100 * \frac{\text{ABSOLUTE VALUE (EHRT - MRT)}}{\text{EHRT}}$$       ! EHRT=EXPECTED HISTORICAL RETENTION
                                                                                  ! TIME
                                                                                  ! MRT=MEASURED RETENTION TIME 921    AVG_SHIFT=AVG_SHIFT + X                 ! ADD VALUE FOR THIS PEAK TO SUM OF
                                               ! PERCENTAGE SHIFTS OF ALL PEAKS FOUND
                                               ! IN THE VARIABLE AVG_SHIFT 922    X > MAXIMUM_SHIFT ?                     ! COMPARE VARIABLE MAXIMUM_SHIFT
                                               ! WITH ABSOLUTE VALUE FOR SHIFT FOR
                                               ! THIS PEAK AND REPLACE MAXIMUM
                                               ! SHIFT AS GREATER VALUES ARE FOUND

923    GO TO 910

1000   COMPUTE AVG_SHIFT = $\frac{\text{AVG\_SHIFT}}{(\text{\# OF REQUIRED PEAKS FOUND})}$ 1001   COMPARE MAXIMUM_SHIFT AND AVG_SHIFT AND TAKE
       THE "SHIFT" VALUE THE GREATER OF 2 TIMES MAXIMUM
       OR 4 TIMES AVG_SHIFT

FIG. 10

|  |  | HISTORICAL<br>RT IN MIN |  | ACTUAL<br>RT IN MIN |
|---|---|---|---|---|
| OPTIONAL MATCH FOR STDPEAK#: | 1 | RT: 1.579 | FROM RAW PK#: | 2 AT 1.576 |
| OPTIONAL MATCH FOR STDPEAK#: | 2 | RT: 2.35 | FROM RAW PK#: | 6 AT 2.345 |
| OPTIONAL MATCH FOR STDPEAK#: | 6 | RT: 6.561 | FROM RAW PK#: | 27 AT 6.559 |
| OPTIONAL MATCH FOR STDPEAK#: | 7 | RT: 7.466 | FROM RAW PK#: | 33 AT 7.489 |
| OPTIONAL MATCH FOR STDPEAK#: | 8 | RT: 8.303 | FROM RAW PK#: | 39 AT 8.408 |
| OPTIONAL MATCH FOR STDPEAK#: | 9 | RT: 9.795 | FROM RAW PK#: | 49 AT 9.793 |

| STD PK #J | FINAL CANDIDATES<br>PERMS (J) | RAW PK #<br>FINAL (J,L) | 1ST CANDIDATE | 2ND CANDIDATE |
|---|---|---|---|---|
| 1 | 2 | 1 | 1.516 | 1.576 |
| 2 | 1 | 6 | 2.345 |  |
| 3 | 1 | 11 | 3.401 |  |
| 4 | 1 | 13 | 3.815 |  |
| 5 | 1 | 14 | 3.961 |  |
| 6 | 1 | 27 | 6.559 |  |
| 7 | 1 | 33 | 7.489 |  |
| 8 | 1 | 39 | 8.408 |  |
| 9 | 1 | 49 | 9.793 |  |
| 10 | 1 | 62 | 12.5 |  |

1ST PERMUTATION FULLMATCH #: 40

| n | c(n) | Rt |
|---|---|---|
| 1 | 1 | 1.516 |
| 2 | 6 | 2.345 |
| 3 | 11 | 3.401 |
| 4 | 13 | 3.815 |
| 5 | 14 | 3.961 |
| 6 | 27 | 6.559 |
| 7 | 33 | 7.489 |
| 8 | 39 | 8.408 |
| 9 | 49 | 9.793 |
| 10 | 62 | 12.5 |

RESULTS OF TOTAL ERROR CALCULATIONS:
FILE 40 ERROR: 0.2977978

2ND PERMUTATION FULLMATCH #: 41

| n | c(n) | Rt |
|---|---|---|
| 1 | 2 | 1.576 |
| 2 | 6 | 2.345 |
| 3 | 11 | 3.401 |
| 4 | 13 | 3.815 |
| 5 | 14 | 3.961 |
| 6 | 27 | 6.559 |
| 7 | 33 | 7.489 |
| 8 | 39 | 8.408 |
| 9 | 49 | 9.793 |
| 10 | 62 | 12.5 |

RESULTS OF TOTAL ERROR CALCULATIONS:
FILE 41 ERROR: 0.0181283

MAX_PERMS: 2     DONE: 2
BEST MATCH=0.0181283
2ND PERMUTATION (41) HAS LEAST TOTAL ERROR AND IS "BEST MATCH"

FIG. 11

METHOD FOR IDENTIFICATION OF COMPONENTS WITHIN A KNOWN SAMPLE

FIELD OF THE INVENTION

The present invention relates to chromatographic analysis systems and, more particularly, to a method and apparatus for identifying components within a known sample through pattern recognition between an array of recognition coefficients representing attributes and stable relationships of historical chromatographic data and similar recognition coefficients representing attributes and stable relationships of a plurality of peaks within a chromatogram of a sample being evaluated.

BACKGROUND OF THE INVENTION

Chromatography is a known method of analyzing a sample comprised of several components to qualitatively determine the identity of the sample components as well as quantitatively determine the concentration of the components.

A typical gas chromatographic apparatus includes an injection port into which the sample is injected and mixed with an inert gas at high temperature, a column through which the various dissolved components of the sample will travel at a rate related to the characteristics of the specific components, and a detector for observing the elution of each component. The time between the injection of a sample and the observed maximum of a peak representing a specific component is called the retention time for that component. The results of a chromatographic separation are displayed as a plot of detector signal versus time, commonly known in the art as a chromatogram. A chromatogram typically comprises a plurality of peaks wherein each peak corresponds to a certain component of the analyzed sample. The area of the peak is to some degree characteristic of the amount of the respective component present in the sample. In order to insure a reliable qualitative and quantitative analysis of the sample, it is necessary that software running on, or in conjunction with the chromatograph, perform proper identification of those peaks in the chromatogram that represent certain compounds present in the sample.

As various components can have different retention times, the chromatogram will usually provide a series of sample peaks wherein each peak represents a respective component in the sample. Ideally, a chromatogram of a sample containing a plurality of components should have a respective plurality of clearly separate and identifiable peaks. Historically, chromatograms have been analyzed to determine the identity of the respective components by noting the time occurrence of the maximum value of each sample peak (retention time) and comparing the observed retention time of a sample peak in the chromatogram to a characteristic retention time for a known, or standard, peak that is derived from a standard mixture of known components. The observed retention time at which each sample peak occurs may be compared to the characteristic retention times of compounds in a standard mixture so as to allow one to assign, or name, an identity to the components in the sample under investigation.

Some conventional chromatographic equipment incorporates peak identification algorithms for improving the process of assigning compound names to the observed chromatographic peaks as a function of the observed retention times. These algorithms are based upon identification of a given peak within a computed retention time window based on one or more adjustable parameters. In particular, if the observed retention time of a given peak in a sample falls within a window centered on a characteristic retention time associated with a compound, the respective compound name is assigned to that peak. If a plurality of peaks occur within the window, the peak nearest the known retention time or the largest peak within the window for the compound is assigned the compound name.

In U.S. Pat. No. 5,905,192, and hereby incorporated by reference, a series of retention time windows are created in accordance with standard peaks. Each retention time window is determined according to the location of its respective standard peak and according to steps for determining one or more shift, stretch, and distort parameters. One or more of the shift, stretch, and distort parameters are used to position each retention time window. The retention time windows are applied in a fashion such that each standard peak is compared to each of the sample peak(s) captured in a given window so as to determine one or more matched pairs of peaks. That is, for each peak in the standard peak group that corresponds to a certain one of the peaks in the sample peak series, a matched pair is determined. A quality factor representing the correspondence of the standard peak to each of the candidate sample peaks in the matched pairs is determined. The resulting quality factors may be compared to determine a best match of the standard peak to one of the candidate sample peaks. The candidate sample peak in the best matched pair is then identified with the compound associated with the respective standard peak. Area percent is also mentioned as a comparison method.

Several shortcomings remain in the above-described approaches. Firstly, they all rely primarily on time domain information, in particular, retention time, for peak identification to succeed. Furthermore, adjustable parameters must be set by those with "some" skill in the practice of chromatography. To increase repeatability over an extended series of separations relatively expensive chromatographic equipment and experienced operators are required to analyze a chromatogram, adjust integration and analysis parameters (including identity parameters) so as to obtain proper identification of sample components.

SUMMARY OF THE INVENTION

Every chromatographic peak has attributes that describe its size, shape and location. While retention time is a location attribute (used extensively in the prior art), the invention provides for the utilization of additional attributes and stable relationships to aid in the identification of unknown components. For example, area and height of a peak are attributes of size; width and symmetry describe a peak's shape, as do algorithmic measures of peak type. It has been found that the attributes of a desired peak (including retention time) are not strictly independent, and may interact. The invention uses functions (which may be non-linear) of several variables to describe how the attributes (by which a desired peak can be recognized) may vary over an analytical range of interest. Coefficients indicating the relationship of a particular peak with its neighbors are also of utility for identification purposes. A simple example is the relative retention time between peaks (which can be expressed as the coefficient $C_{IJ}=RT_I/RT_J$). The use of such relationship information renders some immunity to the expected experimental problems associated with chromatography that are not addressed by a dependence on retention time alone.

According to the teachings of the present invention, a method is provided for identifying components within a known type of sample through pattern recognition between an array of recognition coefficients generated from the attributes and stable relationships of a plurality of peaks within a chromatogram of a sample to be analyzed and a similar array of recognition coefficients generated from the attributes and stable relationships of a plurality of peaks from a set of one or more historical chromatograms of the known type of sample. The group of attributes include, but are not limited to: retention time, peak shape including symmetry, width and duration, peak size including area and height, and algorithmic measures of peak type. Peak type combines shape and size attributes indicating both the gross appearance of a peak (for example, providing for classification as a solvent peak or as a tangent peak), and fine details such as the starting and ending baseline assignments When identifying components within a sample, the invention relies on the presence of certain required peaks in the sample chromatogram to ascertain the general relationships between desired peaks representing the components of the sample to be identified. Some peaks, perhaps the majority, may not be necessary to identify. For purposes of the invention, those desired peaks that are not considered required, are defined as "optional" peaks where the relationship between them can be expressed as:

$$\text{desired peaks} = \text{required peaks} (\geq 3 \text{ required}) + \text{optional peaks}$$

Thus, the number of optional peaks=desired peaks−required peaks, and a minimum of 3 desired peaks is mandatory for the invention to be used for identifying peaks within a chromatogram. Stable relationships between peaks have been found to include the positioning of various desired peaks relative to each other, and the size and shape attributes of the desired peaks over the analytical range of interest. In the preferred embodiment, the historical chromatograms are of a similar sample (having expected variation), and obtained using a similar chromatographic application as that of the sample currently being analyzed such that, recognition coefficients corresponding to the attributes and stable relationships within the historical data may be matched to an array of recognition coefficients representing attributes and stable relationships of the sample to be analyzed.

In particular, the statistical properties for the attributes and stable relationships for each desired peak to be identified are generated over the analytical range of interest. Statistical properties describe the variation observed. After inspection for and removal of suspicious or pathological data, the verified values are characterized to include ranges, mean values, distributional anomalies and tests for interdependence among the attributes and relationships.

For each type of sample being analyzed and the corresponding chromatographic application, a plurality of required peaks are first identified and then employed to correctly identify any additional optional peaks using the stable relationships, including interpolative and extrapolative measures, existing among all peaks in the historical data. The required peaks include one early and one late in the chromatogram to indicate shift and one or more of the tightest grouping of peaks representing the most demanding and difficult of separations.

In a preferred embodiment, peaks are selected based on the extremes among the components as a percentage difference between retention times. For example, for the simplest pair case:

$$\frac{RT_J - RT_I}{0.5 \times (RT_J + RT_I)}$$

In another preferred embodiment, peaks are chosen to represent different thermal profiles. For isothermal chromatographic runs, peak selection is biased towards those peaks that elute later in the run as there is no need to represent multiple thermal profiles.

In another preferred embodiment, groups of peaks are additionally chosen based on the stability of their composition in the sample, on the basis of area, height, or percentages thereof.

To become a "candidate" for consideration as a required peak or an optional peak, an unidentified peak within a sample chromatogram to be analyzed must meet the requirements established for peak attributes and stable relationships at its specific placement within the analytical range of interest. Each candidate peak is screened with respect to the historical data which includes the extremes and expectation values for each attribute. If a candidate's attributes and stable relationships are within the tolerances from the historical data, then it will be considered further. For each desired peak, there may be from none to a large number of candidates identified for further consideration.

The relationships amongst candidate choices for required peaks and optional peaks are employed for selecting the best matches. Several functions are used, including retention time, and where possible, composition. The selection is made using functions of retention time for the computation of a retention time error evaluation function for all the selected candidate peaks. This selection operation is performed twice; first to select the best matches of required peaks, and again when the optional peaks are determined. These functions are linear combinations of retention time differences and retention time ratios. The results of the calculations based on these functions are employed for ascertaining which of the potential required and optional peak candidates in the sample chromatogram have the best match to the historical data. In particular, the results of these calculations are employed for generating a shift factor corresponding to the maximum error found between the observed retention times of the identified required peaks and the historical data. Based on this shift factor, it is possible to identify optional peaks using the amount of shift determined for this particular chromatogram to assist with interpolation and extrapolation from the found required peaks. The closest match is defined as that set of peak candidates having the least total error based on the error evaluation function as applied to all desired peaks found (required and optional peaks). In particular, a series of error calculations are conducted for the combination of permutations of possible required and optional peak retention times as found in the chromatogram, with the minimum error being the best choice. The set of desired peaks that results in the least total error are then identified as the best peak choices. When suitably stable composition data permits, an error evaluation function for composition of the required peaks can be used as an additional confirmation tool when deciding among candidates for the required peaks. Ambiguity is allowed and disclosed; for example, should there be more than one possible optional choice, each having comparable error values, then each optional peak choice would be identified as a possible result, or in another embodiment, ranked by the error value (the less the error, the more "likely" the correct candidate).

BRIEF DESCRIPTION OF THE DRAWINGS

FIG. 4A is an array of the extremes and average values for several attributes of the recognition coefficients for ten desired peaks which are derived from the chromatogram in FIG. 2.

FIG. 4B illustrates a sample of historical data for one of ten desired peaks, some statistical properties derived from the data, and the interaction relationships for several of the peak attributes.

FIG. 4C illustrates the method steps required to generate the data displayed in FIG. 4B.

FIG. 5 is an array of extremes and average values for several attributes corresponding to six required peaks which were selected from the array set forth in FIG. 4A.

FIG. 6 is an array of attributes from twelve peaks which represent run data from the chromatogram illustrated in FIG. 2.

FIG. 7 is a flowchart of a first preferred embodiment of the algorithm for identifying required peaks.

FIG. 8 is a flowchart of a second preferred embodiment of the algorithm for identifying required peaks.

FIG. 10 illustrates the calculations employed for generating a shift specification employed for computing a set of limits for identifying the remaining optional peaks. The shift is derived from required peaks found in a sample.

FIG. 11 is a listing of the final choice permutations that represent the set of required and optional peaks having the least total error.

DETAILED DESCRIPTION OF THE PREFERRED EMBODIMENTS

Figure 1A:
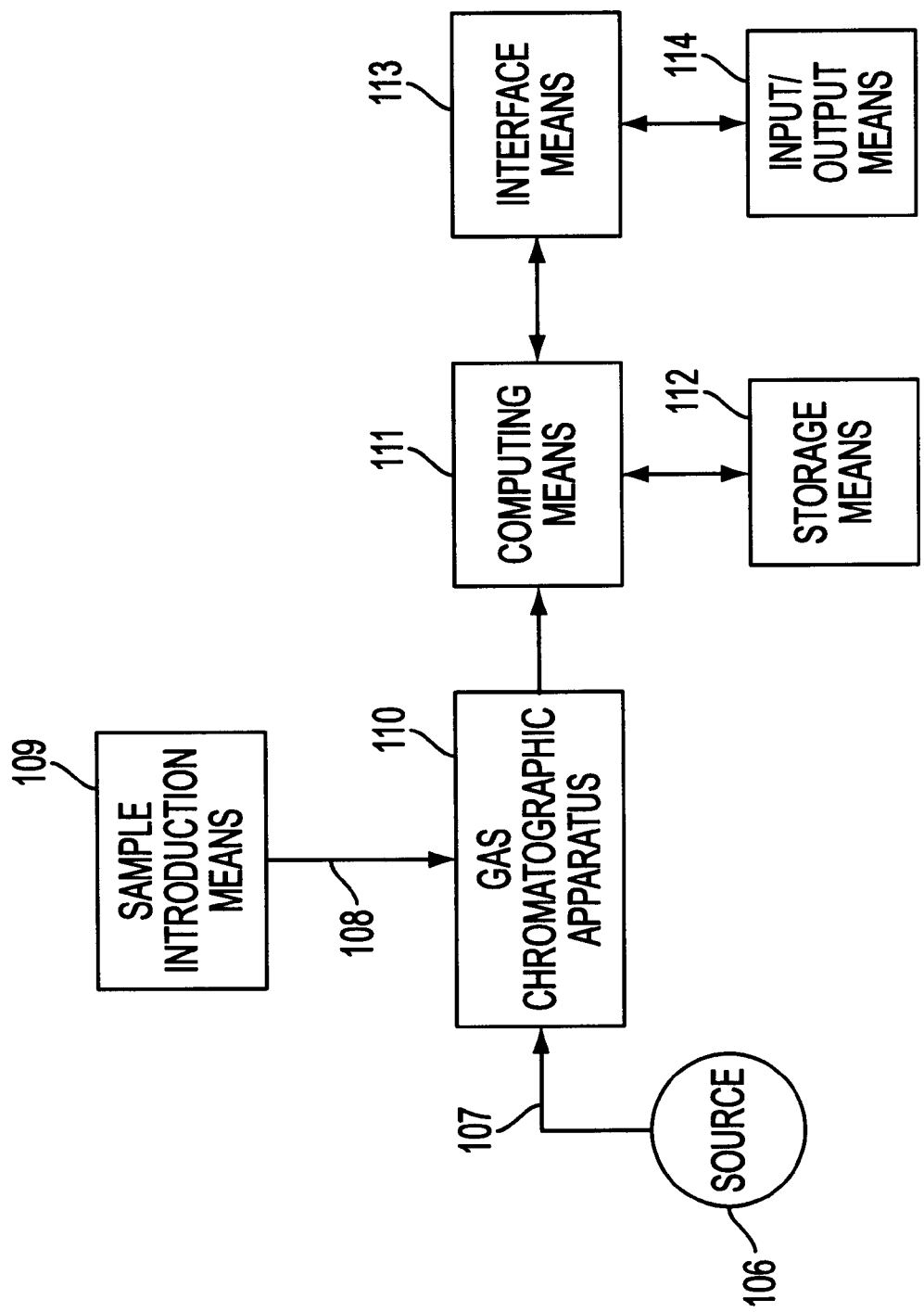
FIG. 1A is a block diagram of a prior art analytical apparatus suitable for the practice of the present invention.

The method of the present invention may be employed to improve the identification of unknown compounds in a known sample present in a fluid in an analytical chromatographic system. Such fluid is intended to include gases, liquids, multiple component gases and liquids, and mixtures thereof capable of unidirectional flow. Gases are the preferred fluids according to the practice of the present invention, and therefore the following description of the invention will be directed to a gas chromatographic analytical system. However, it should be understood that the teachings herein are applicable to chromatographic analysis of gases, liquids, and other compressible fluids.

Every chromatographic peak has attributes and stable relationships that describe its size, shape and location. For example, retention time is a location attribute used extensively in the prior art. Other attributes and stable relationships exist that can aid in identification of unknown components. Area and height of a peak are attributes of size. Width and symmetry describe a peak's shape, as do algorithmic measures of peak type. The attributes of a desired peak including retention time may not be strictly independent but may interact. This invention uses functions (possibly non-linear) of several variables to describe how the attributes (by which a desired peak can be recognized) may vary over an analytical range of interest. Relationships with neighboring peaks are also an important contributor to identification, for example the relative retention time between peaks can be expressed as the coefficient $C_{IJ}$, such as $C_{IJ} = RT_I/RT_J$.

According to the teachings of the present invention, a method is provided for identifying unknown components within a known type of sample through pattern recognition between an array of recognition coefficients corresponding to the attributes and stable relationships of a plurality of peaks within a chromatogram to be analyzed and an array of recognition coefficients corresponding to the attributes and stable relationships of a plurality of peaks from a set of one or more historical chromatograms of the known type of sample. For each type of sample being analyzed in accordance with a specific chromatographic application, a plurality of required peaks are first identified and then employed to correctly identify any additional optional peaks using the stable relationships existing among all desired peaks in the historical data. The relationships of the required peaks to other peaks in the chromatogram is employed to assist in identifying the optional peaks via several means. First, a shift factor is computed to provide help in generally locating all the optional peaks by setting limits specific to shift found in this particular sample. Second, computations specific to each particular optional peak are made using relationships to nearby required peaks to further assure that correct candidates are chosen for consideration as optional peaks. Computation methods employed include interpolation and extrapolation.

Figure 1B:
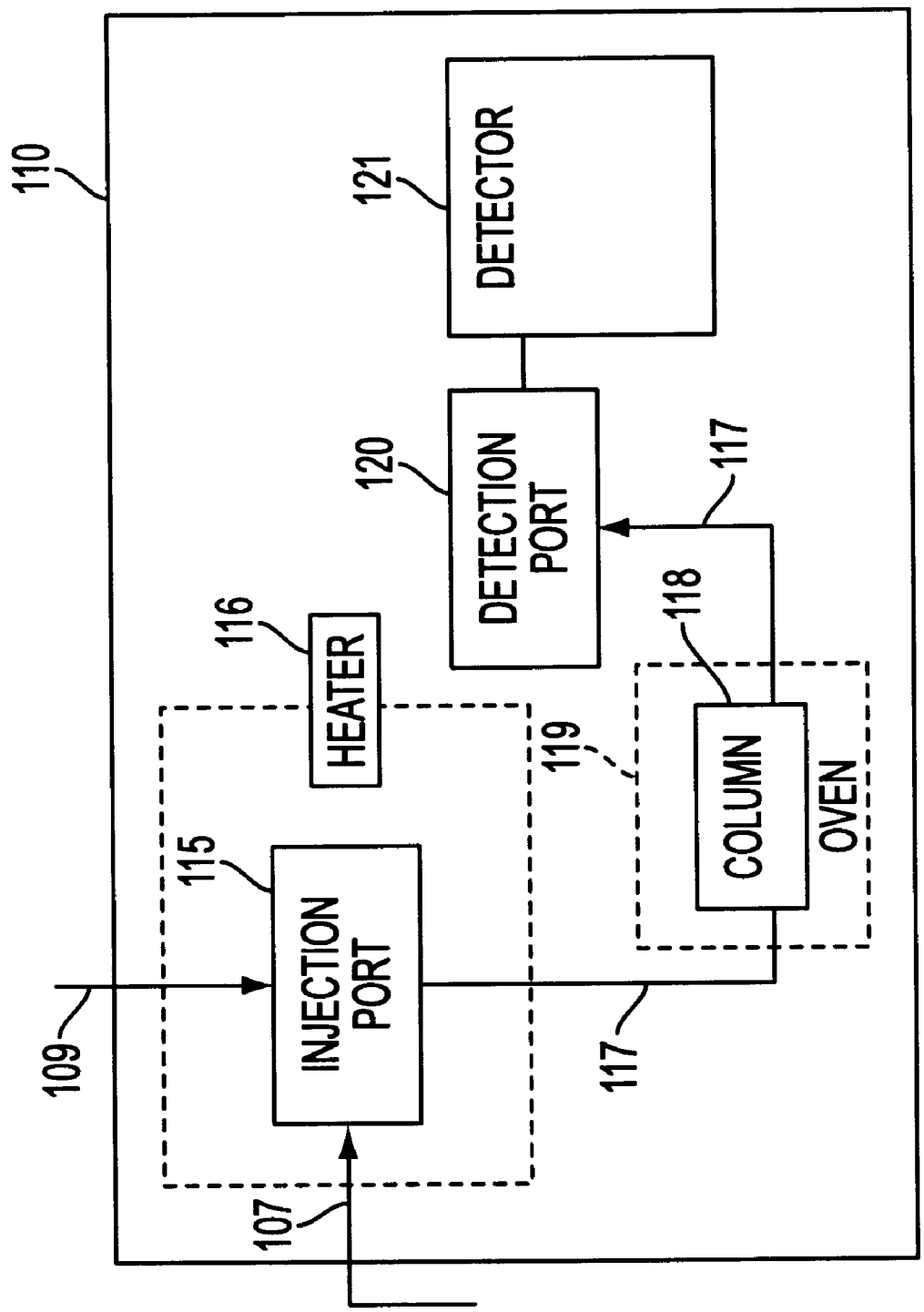
FIG. 1B is a block diagram of a prior art gas chromatographic apparatus which may be utilized with the apparatus of FIG. 1.

A preferred embodiment of an analytical instrument system is illustrated in FIGS. 1A and 1B and includes a source of carrier gas 106, such as hydrogen, nitrogen, of helium—depending upon the particular chromatographic seperation to be performed, a sample introduction means 109, a gas chromatographic apparatus 110 Inlet lines 107 and 108 provides carrier gas and samples respectively to the chromatographic apparatus 110. The analytical instrument system further includes a, computing means 111, storage means 112, interface means 113, and input/output means 114. In order to perform a chromatographic separation of a sample a quantity of the sample is injected into an injection port 115 that is supplied with carrier gas stream 117. The injection port 115 has an associated heater 116. The injection port 115 provides a portion of the sample/carrier gas mixture to a separation column 118 in a column oven 119.

As the carrier gas (containing the sample) exits the column 118, the presence of one or more sample constituent components passes through a detection port 120 and is detected by a detector 121. The detector output signal is then received by the computing means 111 and optionally stored in the storage means 112. Preferably, the detector output signal is provided in the form of data representative of a series of sample peaks in at least one chromatogram. The system may be operated according to a preferred embodiment of a peak identification method according to one or more programs operable in the computing means 111.

Figure 2:
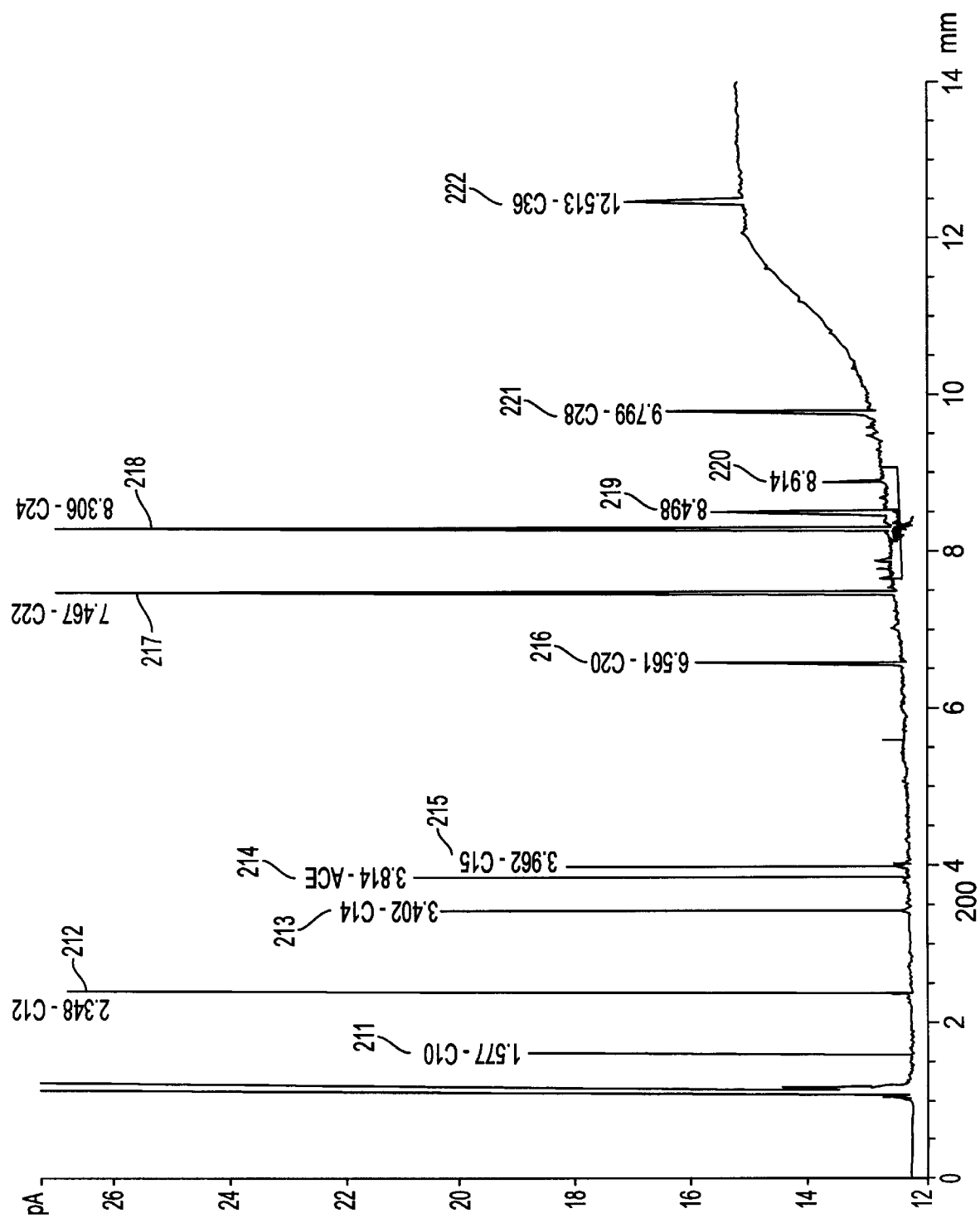
FIG. 2 is an actual chromatogram of a synthetic hydrocarbon mixture having twelve chromatographic peaks, ten of which are identified as C10–C36 hydrocarbons.
Figure 3:
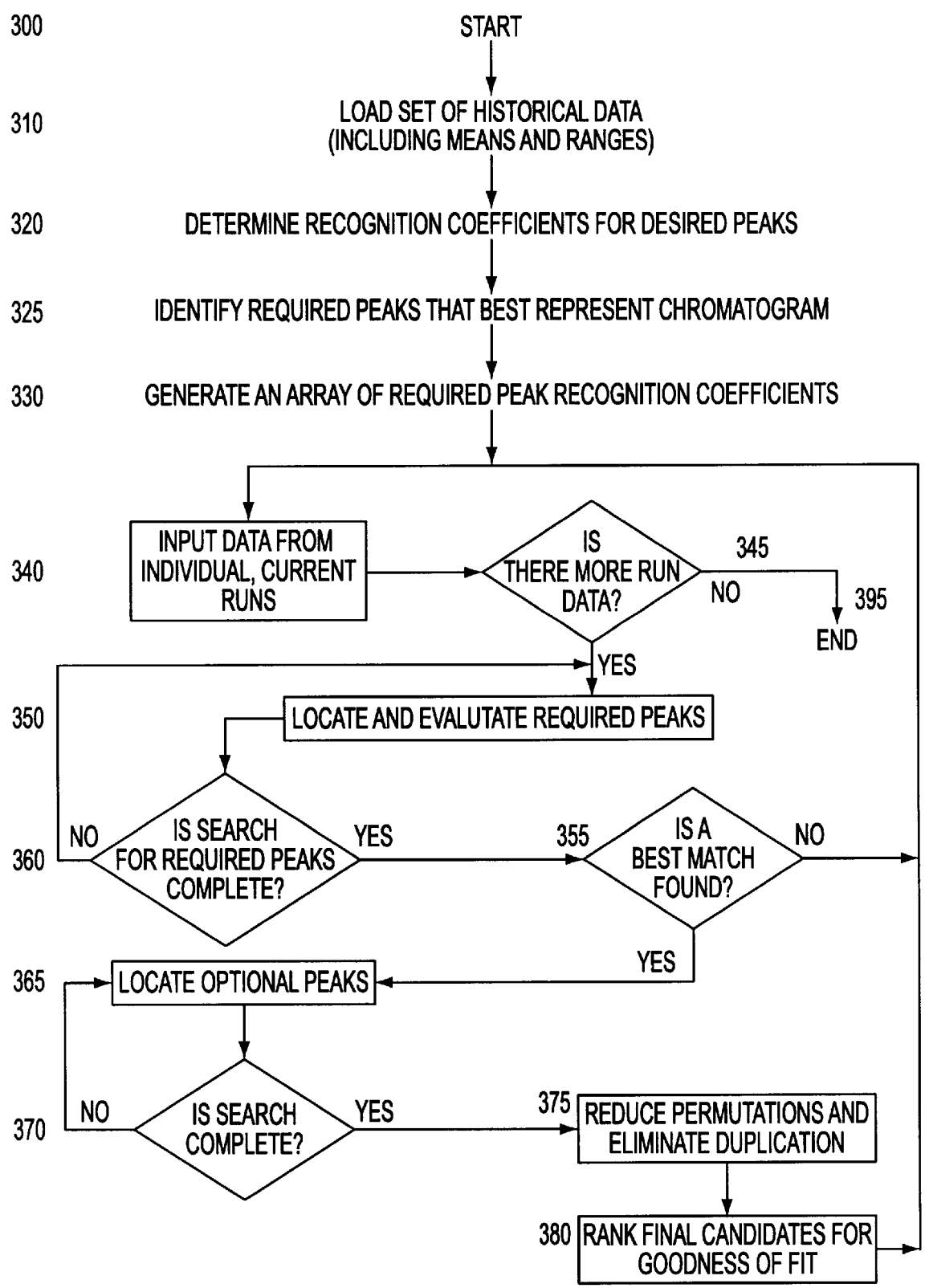
FIG. 3 is flowchart depicting an algorithm for identification of chromatographic peaks in accordance with the invention.

FIG. 2 is a chromatogram of a known sample (a synthetic hydrocarbon mixture) having many components, each represented by a peak (211–222) of which ten are desired peaks (211–218, 221, 222) as they represent hydrocarbons. FIG. 3 is a flowchart illustrating the method steps of the invention for identifying the desired peaks and starts step 300 and ends with step 395. In particular, at step 310, historical data derived from one or more chromatograms of chromatographic separations and identifications on a known type of sample (in accordance with a specific chromatographic application) is referenced. At step 320, each of the ten desired peaks within the historical data is characterized by a plurality of recognition coefficients based on the attributes of the peak that describe its size, shape and location, including: retention time, peak shape including symmetry, width and duration, peak size including area and height, and algorithmic measures of peak type, as well as the stable relationships between pairs or groups of peaks. At this time, statistical properties, as described previously, are examined and saved. The computing means 111 (FIG. 1) is programmed by one skilled in the art to generate these coefficients and properties and store them in the storage means (data box) 112. FIG. 4A is the "attribute" portion of an array of recognition coefficients based on historical data for the ten desired peaks numbered J:1 through J:10 (corresponding to the peaks 211–218, 221, 222 identified in FIG. 2), and includes the mean and the extreme values for each peak as received (or estimated, if necessary) from the database of historical data. FIG. 4B illustrates the historical data summary for Peak 8, including statistical properties, statistical measures of dispersion and coefficients indicating goodness of fit for linear and non-linear functions describing how attributes interact over the analytical range of interest.

While the invention provides for accessing the database of historical recognition coefficients that is generated by analyzing a series of chromatographic runs of a similar sample, it is also possible to generate an "intelligent" database that makes reasonable interpolations and extrapolations based on its limited knowledge using the results of a sample chromatogram to update the database for identifying components in future chromatographic runs. As the variety of chromatographic runs is increased, the invention provides increased robustness in accordance with increasing statistical confidence.

At step 325, a number of required peaks (a subset of the desired peaks) are identified that best represent the chromatogram. The required peaks provide for the identification of optional peaks based on their known relationships to the required peaks. The required peaks include one early and one late in the chromatogram to represent drift, and one or more of the tightest group of peaks representing the most difficult chromatographic separation amongst sample components.

In a preferred embodiment, some required peaks are selected based on the extremes among the components as a percentage difference between retention times. For example, for the simplest pair case:

$$\frac{RT_{(J)} - RT_{(I)}}{.5 \times RT_{(J)} + RT_{(I)}}$$

One or more required peaks are also chosen to represent different thermal profiles. For isothermal chromatographic runs, required peak selection is biased towards those peaks that elute later in the run as there is no need to represent multiple thermal profiles.

In another preferred embodiment, the required peaks are chosen by picking: (1) the first and last of the desired peaks, (2) one or more peaks representing the thermal profile of the chromatographic run (thus, at least one in the isothermal stage, and at least one in the temperature programmed stage), (3) one or more peaks based on the tightest "pairing" of groups of two or more peaks as a percentage of their retention time and (4) where stability of the compositional relationships permits, peaks are selected that exhibit the highest degree of stability and correlation with each other.

An array of attribute recognition coefficients (a subset of the historical data) corresponding to the required peaks is selected at step 330. FIG. 5 shows a subset of data from FIG. 4, and illustrates the attribute portion of the recognition coefficients representing historical data for the six required peaks identified in FIG. 2 (211, 213, 214, 215, 218 and 222). These required peaks aim to provide a valid representation of the entire chromatogram such that optional peaks (those desired peaks that are not required peaks, or could not be positively identified as required peaks) can be identified using computations including interpolations and extrapolations with the required peaks and the historical data. For example, one would not typically pick only the first three peaks of a multipeak chromatogram to assist in the identification of the last three peaks as the first three peaks may not typically exhibit the same behavior and experimental influences as the other peaks in the chromatogram.

REQUIRED PEAK IDENTIFICATION

At step 340, chromatographic "run data" (therefore, a chromatogram) corresponding to the sample containing components to be identified is input in the computer 111. (FIG. 6 represents the attributes (retention time, peak type, symmetry, area, width, height, baseline value and duration) generated by the computer 111 based on the run data illustrated in FIG. 2. At step 345, a decision is made whether any new data exists, if yes, the data from the sample chromatogram is screened for tolerance within selected attributes of the required peaks and those passing become candidates to be evaluated for the best match with the historical recognition coefficients of the corresponding peaks (step 350/355). Note that the chromatogram (FIG. 2) has 12 peaks (211–222), so it is not possible to simply identify the 10 desired peaks.

At step 350, the required peak candidates are located and evaluated. At step 360, a decision is made whether the search is completed. If complete, then a decision is made whether a best match between historical data and the set of required peaks has been found, if not, then the requirements for analysis are not met, and there is a return to step 345 and data for another sample is awaited. If a best match has been found, then the process continues at step 365 with the location of the optional peaks. An acceptable set of "required" peaks is a mandatory precondition for step 365.

In particular, the required peaks from the sample chromatogram are screened for being within tolerance for selected attributes. In a first embodiment (set forth in the flowchart of FIG. 7) and beginning with step 700, each sample candidate peak attribute is tested to determine whether it's value is within the expected range of corresponding historical attributes (steps 720–727). In the flowchart of FIG. 7, the required peak counter is set to 0 in step 702 and is incremented during the process by 1 in step 703. In step [703] 704, if the required peak counter is at N+1, the process goes to step 750 and stops. The candidate peak counter is set to 0 for the first peak in step 710. Step 715 sets up a loop for reviewing the attributes of each peak to ascertain whether each peak passes all the screens and is identified as a required peak candidate. For a candidate peak to be considered as a required peak it must pass through every screen (720–727) indicating that every attribute is within the expected range. If it does, that peak is marked as a peak candidate (step 730). If C equals the number of peaks present, then step 740 of the flowchart returns the process to step 703. If not, that peak is discarded and the next potential candidate peak (step 745) is considered as a potential required peak (step 720).

In another preferred embodiment (illustrated in the flowchart of FIG. 8) starting with step 800 [The required peak counter is set to 0 in step 810 and is incremented during the process by step 820. The candidate peak counter is set to 0 for the first peak in step 821. In step 822, if the required peak counter is at N+1, the process goes to step 880 and stops. If the area attribute of a peak is not within limits for required peaks in step 825, the peak is not matched and the process goes to step 823, increments the candidate peak counter by 1. If in step 840, the default setting of attributes identifies required peaks, the process of FIG. 8 goes to step 862. If the area attribute of a peak is outside the normal range for required peaks, step 830 of the process goes to step 850. Peaks that pass the all of the "screens" at step 870 are marked as peak candidates. If a candidate peak meet the attributes of required peak at step 872, the process returns to step 820. The counter for required peaks is incremented by 1. Step 874 goes to step 823 to continue to test peaks that are present. When the process is finished, it stops at step 880] the magnitude of one or more candidate attributes (for example, Area in the example) are employed to precisely define the expected ranges for other attributes (for example, width or retention time). The required peak counter is set to 0 in step 810 and is incremented during the process by step 820. The candidate peak counter is set to 0 for the first peak in step 821. In step 822, if the required peak counter is at N+1, the process goes to step 880 and stops. If the area attribute of a peak is not within limits for required peaks in step 825, the peak is not matched and the process goes to step 823, increments the candidate peak counter by 1. If in step 840, the default setting of attributes identifies required peaks, the process of FIG. 8 goes to step 862. If the area attribute of a peak is outside the normal range for required peaks, step 830 of the process goes to step 850. Peaks that pass the all of the "screens" at step 870 are marked as peak candidates. If a candidate peak meet the attributes of required peak at step 872, the process returns to step 820. The counter for required peaks is incremented by 1. Step 874 goes to step 823 to continue to test peaks that are present. When the process is finished, it stops at step 880. At step 850, a new set of attributes are computed for each required peak based on a non-linear equation having coefficients based on the non linear functions derived from historical data. For example (and with reference to the data set forth in the bottom portion of FIG. 4B):

$$RT = C_a + C_b \times Area + C_c \times Area^2$$

$$WID = C_d + C_e \times Area + C_f \times Area^2$$

$$SYM = C_g + C_h \times Area + C_i \times Area^2$$

The coefficients in the equations above demonstrate interactions between the area and other attributes and are derived through regression analysis. An example of such a non-linear equation for data associated with peak 8 is illustrated, with coefficients $C_1$–$C_9$ at the lower portion of FIG. 4B, in which the interaction of Area with several other attributes for the selected peak is illustrated (the values of area have been mean-centered and scaled since the range of variables is broad). The sample peaks are analyzed sequentially through expected values for attributes and a sample peak is only chosen if it is within the expected ranges of the historical data (steps 862–868). In particular, a required sample peak is chosen as a candidate when it passes all of the "screens". Variance between the historical data and the sample chromatographic data is anticipated and the screens are modified in accordance with the application and accuracy of the system using values of statistical variation. The search criteria may rule out or exclude candidates for certain required peaks due to stringent requirements and tightly controlled screens. All unidentified peaks are free to participate and be found later as an optional peak using modified search criteria, which may be less strict than for required peaks.

The search for best match among the required peak candidates selected using the screens is done by means of a non-linear error evaluation function. This function is similar to the function which will be used later for evaluation of all the desired peaks found (required and optional). The error function is composed of peak and group attributes derived from the historical data and properties, consisting of linear combination of retention time differences and ratios, and composition information from each set of candidates for the required peaks.

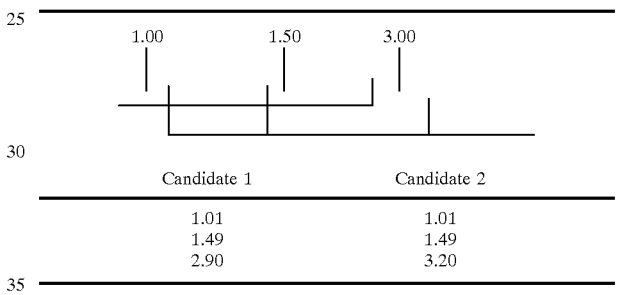

| | Candidate 1 | Candidate 2 |
|---|---|---|
| | 1.01 | 1.01 |
| | 1.49 | 1.49 |
| | 2.90 | 3.20 |

In the foregoing illustration, there are three required peaks with mean retention times of 1.00, 1.50, 3.00 minutes as derived from the historical data. Screening from a sample produces two candidate possibilities for the choice of the final peak, namely, one with a retention time of 2.90 or one with a retention time of 3.20 minutes.

The error function compares retention time differences and retention time ratios among the required peaks such that the poorer the match, the higher the computed error. To achieve this, summations are performed over the squared differences between all found ratios and found difference in accordance with the following equations:

$$R_{IJ} = \frac{(\text{Candidate Retention Time})_I}{(\text{Candidate Retention Time})_J}$$

$$H_{IJ} = \frac{(\text{Historical Data Retention Time})_I}{(\text{Historical Data Retention Time})_J}$$

$$D_{IJ} (\text{Candidate Retention Time})_I - (\text{Candidate Retention Time})_J$$

$$K_{IJ} (\text{Historical Data Retention Time})_I - (\text{Historical Data Retention Time})_J$$

$$\text{Error}_A = \Sigma (R_{IJ} H_{IJ})^2$$

$$\text{Error}_B = \Sigma (D_{IJ} K_{IJ})^2$$

| | | |
|---|---|---|
| $H_{12} = 0.67$ | $K_{12} = 0.50$ | Historical |
| $H_{23} = 0.50$ | $K_{23} = 1.50$ | Data |
| $H_{13} = 0.33$ | $K_{13} = 2.00$ | |

-continued

| | | |
|---|---|---|
| $R_{12} = 0.68$ | $D_{12} = 0.48$ | Candidate |
| $R_{23} = 0.51$ | $D_{23} = 1.41$ | 1 |
| $R_{13} = 0.35$ | $D_{13} = 1.89$ | |
| $R_{12} = 0.68$ | $D_{12} = 0.48$ | Candidate |
| $R_{23} = 0.47$ | $D_{23} = 1.7$ | 2 |
| $R_{13} = 0.32$ | $D_{13} = 2.19$ | |

For Candidate 1

$$E_{1A}=(0.01)^2+(0.01)^2+(0.02)^2=0.0006$$

$$E_{1B}=(-0.02)^2+(-0.09)^2+(-0.11)^2=0.0242$$

For Candidate 2

$$E_{2A}=(0.01)^2+(-0.03)^2+(-0.01)^2=0.0011$$

$$E_{2B}=(-0.02)^2+(0.21)^2+(0.19)^2=0.0806$$

These error terms, $E_A$ and $E_B$, are combined and multiplied by a factor, F, that measures deviation from the expected pattern of translation and duration for the required peaks. In this case $$t = \frac{\text{maximum retention time difference}}{\text{earliest retention time}}$$

$$t_H = \frac{3.00 - 1.00}{1.00} = 2 \qquad F_X = t_H/t_X + t_X/t_H$$

$$t_1 = \frac{2.9 - 1.01}{1.01} = 1.87 \quad F_1 = 2/1.87 + 1.87/2 = 2.005$$

$$t_2 = \frac{3.2 - 1.01}{1.01} = 2.19 \quad F_2 = 2/2.19 + 2.19/2 = 2.008$$

If the variability in the computed value for t is larger compared to that from the historical data, additional tests for the direction of translation and duration are done. Should these tests indicate inconsistent chromatographic behavior, such as a shorter run time with a later starting point, the factor F is increased to include non-linear power terms in t.

$$\text{Error for Candidate } 1 = (E_{1A}+E_{1B}) * F_1 = 0.0497$$

$$\text{Error for Candidate } 2 = (E_{2A}+E_{2B}) * F_2 = 0.164$$

Candidate 1 has significantly lower error. Had this not been the case, composition data, if available, could be used to distinguish the candidate choices in a similar manner.

OPTIONAL PEAK IDENTIFICATION

Referring back to FIG. 3, step 370, a decision is made as to whether the search for optional peaks is finished, if not then return to step 365 to locate any additional optional peaks. This could happen initially if only the required peaks are present. If the search is complete, then go to step 375 to reduce the permutations, if any, and eliminate duplicate candidates. At step 380, and as illustrated in FIG. 11, each permutation of required and optional peaks (particularly, optional peak candidates) are analyzed to ascertain which set provides the least total error based on the error evaluation function as applied to all peaks (required and optional peaks).

Optional peak candidates from the sample chromatogram are similarly screened with a screening process based on retention time of the optional peak candidates and the stable relationships to the required peaks for which retention times have been identified, and the corresponding retention time of the optional and required peaks as set forth in the historical data. The computation means employed include interpolation where possible and extrapolation, if necessary.

As previously set forth in regards to identifying the required peaks, the total error function and the calculations performed supporting both difference analysis and ratio analysis between peaks is employed for identifying those optional peaks providing the best match. In particular, candidates are selected for the optional peaks on the basis of specific stable relationships to neighboring bracketing pairs selected from the required peaks. In the simplest case, interpolation between adjacent (bracketing) reference peaks can be used. The computed shift error (see FIG. 10) is used to adjust the values. As shown in FIG. 10, step 901 AVG_SHIFT is reset to 0. In step 902 the MAXIMUM_SHIFT is reset to 0 and in step 903 the REQUIRED_PEAK_COUNT is reset to 0. Step 910 loops for all the REQUIRED_PEAK_COUNT. Step 911 goes to step 1000 to compute AVE_SHIFT, if the REQUIRED_PEAK_COUNT>the LAST_REQUIRED_PEAK. If the REQUIRED_PEAK is not found, step 912 goes to step 910. For each REQUIRED_PEAK found, step 920 computes the absolute value as percentage for the peak:

$$X = 100 * \frac{\text{ABSOLUTE VALUE } (EHRT - MRT)}{EHRT}$$

Where:

$EHRT$ = EXPECTED HISTORICAL RETENTION TIME and $MRT$ = MEASURED RETENTION TIME

Step 921 performs the step of AVE_SHIFT=AVG_SHIFT+ x. If required, step 923 goes to step 910. Step 1000 performs:

$$\text{COMPUTEAVG\_SHIFT} = \frac{\text{AVE SHIFT}}{(\text{\#OF REQUIRED PEAKS FOUND})}$$

And step 1001 compares MAXIMUM_SHIFT and AVG_SHIFT and takes the "SHIFT" value the greater of 2 times maximum or 4 times AVG_SHIFT. Any peaks not positively identified as required peaks become search targets as optional peaks.

Figure 9:
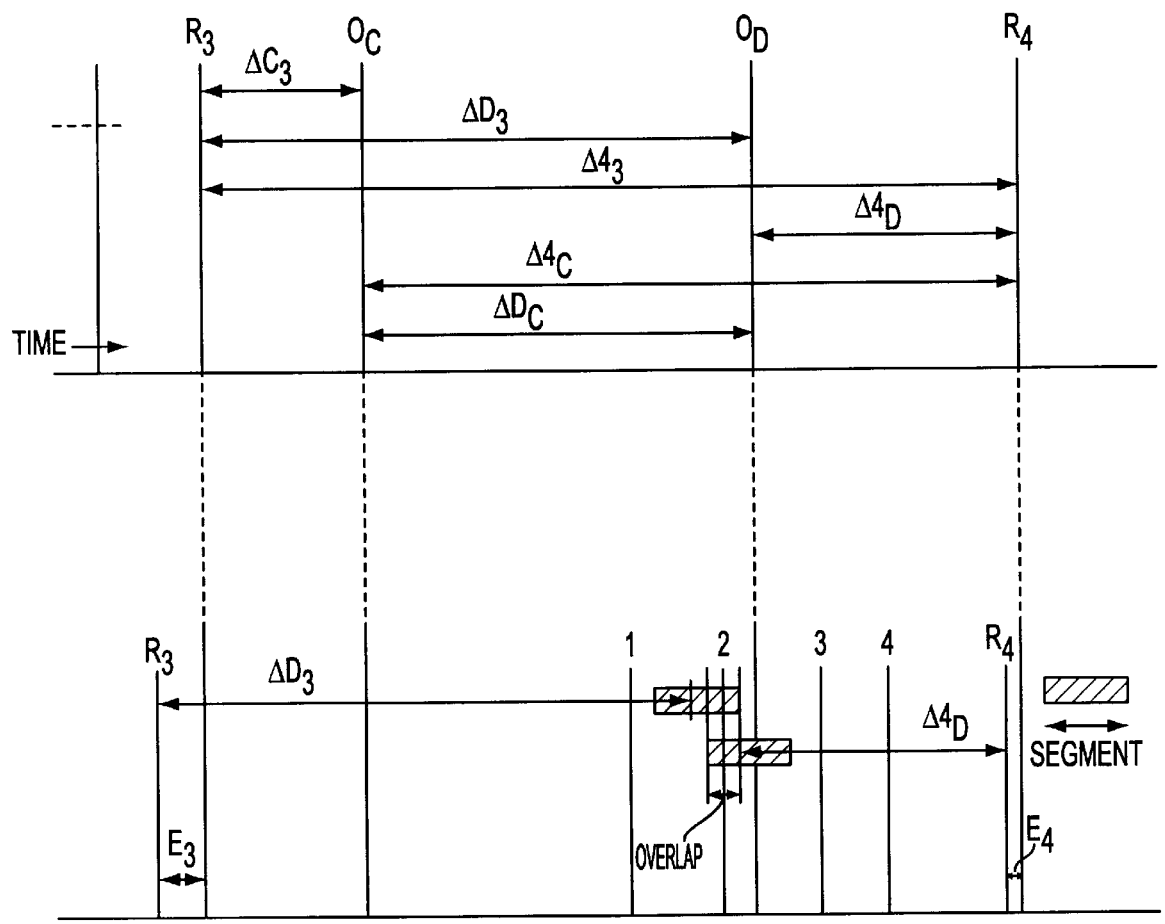
FIG. 9 illustrates and explains the relationship calculations performed supporting both difference analysis and ratio analysis among the desired peaks.

The difference in retention time (RT) between each optional peak and the two closest identified required peaks that bracket the corresponding optional peak are made with respect to the retention time of each identified required peak and each possible optional peak. The upper portion of FIG. 9 illustrates the case of interpolation between adjacent bracketing or required peaks ($R_3$, $R_4$) for the optional peak, $O_D$ (where optional peaks $O_C$, $O_D$) are indicated for historical data. Among the recognition coefficients are the retention time differences between each desired peak. For the optional peak, $O_D$, these include:

$\Delta_{D3}$—the difference between $O_D$ and $R_3$ $\Delta_{4D}$—the difference between $R_4$ and $O_D$, and $\Delta_{DC}$—the difference between $O_D$ and $O_C$ as well as many others not illustrated.

The lower portion of FIG. 9 illustrates an unknown sample in which the required peaks $R_3$ and $R_4$ have been located and four candidates are being considered for peak $O_D$. Also shown are the individual errors for located required peaks ($E_3$, $E_4$ shown here) which are combined to produce a shift value, indicated by the segment S, indicating a shift for this particular sample (see FIG. 10). The shift value is applied as a fractional multiplier to the combination of retention times used for the difference values. Graphically, this is a region (shaded) added to the $\Delta_{D3}$ and $\Delta_{4D}$ values where interpolation is allowed. The overlap of these two regions, indicated in FIG. 9, designates candidate peak 2 as meeting both the conditions for interpolation. While only two reference peaks are employed in this example, the use of additional reference peaks can provide further designation and increase certainty, if necessary.

The ratio of the retention times between each peak pair and the difference between each possible pair of peaks are made with respect to the retention time of each identified required peak and each possible optional peak. The results of these calculations as just described are employed for ascertaining which of the potential optional peaks in the inputted chromatogram can qualify as candidates. After elimination of duplicate and out of order permutations, a non-linear error function as previously set forth in regards to required peak candidates is used to compare choices and get the best "match" from several optional peak candidates. Illustrated in FIG. 11 are two optional peak permutations for the historical peak at 1.579. Each choice is evaluated in turn, and the choice of 1.576 for the candidate has the lower error, 0.0181 being lower then 0.297.

The examples illustrate the invention employed for identifying components within a mixture of hydrocarbons. However, the invention may be employed for most any type of repeated chromatographic application in which historical data (at least one set) is available. The use of patterns in identification provides for the reduction in the dependence on precise hardware by allowing chromatograms to shift and still properly identify the components in a sample, and with appropriate sets of historical data, the invention reduces dependence on adjustable parameters to obtain useful results. By communicating information on the magnitude and direction of shift computed for various groups of peaks, the invention can provide stabilization and control for properly designed chromatographic hardware.

Where historical data is available for different (alternative) types of samples, and where this historical data shows statistically distinguishable attributes and coefficients, the invention may advantageously be employed for classifying an unknown sample as one of several alternatives, by ranking its similarity using the previously described numerical match criteria.

What is claimed is:

1. A method for identifying components within a known type of sample through pattern recognition between an array of recognition coefficients corresponding to the attributes and stable relationships of a plurality of desired peaks within a chromatogram to be analyzed and an array of recognition coefficients corresponding to the attributes and stable relationships of a plurality of desired peaks from a set of historical chromatograms of the known type of sample, comprising the method steps of:

deriving an array of recognition coefficients from one or more historical chromatograms, the array of recognition coefficients corresponding to attributes, stable relationships and statistical properties of each desired peak in the historical chromatogram analyzed, each peak or groups of peaks representing known components of the known sample, selecting a plurality of required peaks from all of the desired peaks, the required peaks characterizing the chromatogram so as to provide for the identification of optional peaks through their relationships with the required peaks; and selecting one or more optional peaks from the chromatogram aided by adjustment of expected behavior of the optional peaks and from a total error function based on the retention times of the required peaks, the optional peaks and the retention times of the desired historical peaks, wherein a minimum of three desired peaks are used for identifying peaks within a chromatogram.

2. The method for identifying unknown components within a known sample as claimed in claim 1, the array of recognition coefficients further comprising one or more of the group of characteristics including:

retention time, peak shape including symmetry, area of each peak as a percent of all peak areas, the height and width of a peak and peak type.

3. The method for identifying unknown components within a known sample as claimed in claim 1, the array of recognition coefficients further comprising the statistics to include ranges of uncertainty, extremes of minimum and maximum, and measures of dispersion (moments) and central tendency (mean, median) of each recognition coefficient for a minimum of at least three required peaks.

4. The method for identifying unknown components within a known sample as claimed in claim 1, the required peaks further comprising, the first and last peak of the chromatogram, one or more peaks representing the thermal profile of the chromatographic run, and one or more peaks based on the tightest "pairing" of groups of two or more peaks as a % of their retention time.

5. The method for identifying unknown components within a known sample as claimed in claim 4, the one or more peaks representing the thermal profile of the chromatographic run further comprising at least one peak in an isothermal stage, and at least one peak in a temperature programmed stage.

6. The method for identifying unknown components within a known sample as claimed in claim 1, the error evaluation function further comprising the step of calculating, with respect to the retention time of each identified required peak: (1) the difference in runtime (RT) between each required peak, (2) the ratio of the retention times between each pair of peaks, and (3) the difference between each pair of peaks, wherein the results of these calculations are employed for ascertaining which of the potential optional peaks in the inputted chromatogram have the best match to the historical data.

7. The method for identifying unknown components within a known sample as claimed in claim 6, further comprising:

generating a shift factor corresponding to the greatest possible error found between the actual retention times of the identified required peaks and the historical data; and identifying optional peaks which once "shifted", have the "closest match" to the historical data, wherein the closest match is defined as those peaks having the least total error based on the error evaluation function as applied to all peaks (required and optional peaks).

8. The method for identifying unknown components within a known sample as claimed in claim 7, further comprising;

the step of conducting a series of total retention time error calculations for the combination of all permutations of possible optional peak retention times as set forth in the chromatogram as compared to the mean of the historical data, and the total errors of the required peaks in relationship to the mean of the historical data; and identifying the optional peaks as the set of optional peaks that in combination with the required peaks, results in the least total error.

9. The method for identifying components within a known type of sample through pattern recognition, as claimed in claim 8, further comprising the step of computing a retention time error evaluation function for all the selected candidate peaks, wherein, this selection operation is performed twice; first to select the best matches of required peaks, and again when the optional peaks are determined, and wherein, these functions are linear combinations of retention time differences and retention time ratios, and wherein, the results of the calculations based on these functions are employed for ascertaining which of the potential required and optional peak candidates in the sample chromatogram have the best match to the historical data.

10. The method for identifying components within a known type of sample through pattern recognition, as claimed in claim 7, the step of generating a shift factor corresponding to the maximum error found between the observed retention times of the identified required peaks and the historical data, further comprising the step of identifying the optional peaks using the amount of shift determined for this particular chromatogram to assist with interpolation and extrapolation from the found required peaks, the closest match is defined as that set of peak candidates having the least total error based on the error evaluation function as applied to all desired peaks found (required and optional peaks).

11. A method for identifying components within a known type of sample through pattern recognition between an array of recognition coefficients that describe the size, shape and location of a plurality of desired peaks within a chromatogram to be analyzed and an array of recognition coefficients corresponding to the attributes and stable relationships of a plurality of desired peaks from a set of historical chromatograms of the known type of sample, comprising the method steps of:

describing how the attributes may vary over an analytical range of interest, wherein the method step of describing further comprises indicating the relationship of a particular peak with its neighbors, identifying certain required peaks in the sample chromatogram to ascertain the general relationships between desired peaks representing the components of the sample to be identified, including interpolative and extrapolative measures, existing among all peaks in the historical data, and wherein, those desired peaks that are not considered required, are defined as "optional" peaks, the number of optional peaks=desired peaks—required peaks, and a minimum of 3 desired peaks is mandatory for the invention to be used for identifying peaks within a chromatogram, identifying the optional peaks using the stable relationships between the required peaks, wherein the recognition coefficients corresponding to the attributes and stable relationships within the historical data may be matched to an array of recognition coefficients representing attributes and stable relationships of the sample to be analyzed, generating over the analytical range of interest, the statistical properties for the attributes and stable relationships for each desired peak to be identified, characterizing the statistical properties to include ranges, mean values, distributional anomalies and tests for interdependence among the attributes and relationships.

12. The method for identifying components within a known type of sample through pattern recognition, as claimed in claim 11, the step of identifying the required peaks further comprising selecting peaks based on the extremes among the components as a percentage difference between retention times.

13. The method for identifying components within a known type of sample through pattern recognition, as claimed in claim 11, the group of described attributes including: retention time, peak shape including symmetry, width and duration, peak size including area and height, and algorithmic measures of peak type.

14. The method for identifying components within a known type of sample through pattern recognition, as claimed in claim 13, wherein, peak type combines shape and size attributes indicating both the gross appearance of a peak and fine details including the starting and ending baseline assignments.

15. The method for identifying components within a known type of sample through pattern recognition, as claimed in claim 11, the step of identifying the required peaks further comprising identifying peaks to represent thermal profiles, and wherein, for isothermal chromatographic runs, peak selection is biased towards those peaks that elute later in the urn as there is no need to represent multiple thermal profiles.

16. The method for identifying components within a known type of sample through pattern recognition, as claimed in claim 11, the step of identifying the required peaks further comprises the step of identifying peaks based on the stability of their composition in the sample, on the basis of area, height, of percentages thereof.

17. The method for identifying components within a known type of sample through pattern recognition, as claimed in claim 11, the step of identifying the required peaks further comprises the step of identifying that meet the requirements established for peak attributes and stable relationships at its specific placement within the analytical range of interest, wherein, each candidate peak is screened with respect to the historical data which includes the extremes and expectation values for each attribute, and wherein, if a candidate's attributes and stable relationships are within the tolerances from the historical data, then it will be considered further, and wherein, for each desired peak, there may be from none to a large number of candidates identified for further consideration.

18. The method for identifying components within a known type of sample through pattern recognition, as claimed in claim 17, further comprising the step of selection the best matches between required peaks and optional peaks based on the relationships amongst candidate choices, including retention time, and where possible, composition.

19. The method for identifying components within a known type of sample through pattern recognition, as claimed in claim 18, further comprising the step of computing a retention time error evaluation function for all the selected candidate peaks, wherein, this selection operation is performed twice, first to select the best matches of required peaks, and again when the optional peaks are determined, and wherein, these functions are linear combinations of retention time differences and retention time rations, and wherein, the results of the calculations based on there functions are employed for ascertaining which of the potential required and optional peak candidates n the sample chromatogram have the best match to the historical data.

20. The method for identifying components within a known type of sample through pattern recognition, as claimed in claim 19, further comprising the step of generation a shift factor corresponding to the maximum error found between the observed retention times of the identified required peaks and the historical data, and further comprising the step of identifying the optional peaks using the amount of shift determined for this particular chromatogram to assist with interpolation and extrapolation from the found required peaks, the closest match is defined as that set of peak candidates having the least total error based on the error evaluation function as applied to all desired peaks found (required and optional peaks).

21. The method for identifying components within a known type of sample through pattern recognition, as claimed in claim 20, further comprising the step of conduction a series of error calculations for the combination of permutations of possible required and optional peak retention times as found in the chromatogram, with the minimum error being the best choice, wherein, the set of desired peaks that results in the least total error are then identified as the best peak choices.

22. The method for identifying components within a known type of sample through pattern recognition, as claimed in claim 21, wherein suitably stable composition data permits, an error evaluation function for composition of the required peaks can be used as an additional confirmation tool when deciding among candidates for the required peaks.

23. The method for identifying components within a known type of sample through pattern recognition, as claimed in claim 21, wherein, should there be more than one possible options choice, each having comparable error values, then each options peak choice would be identified as a possible result.

* * * * *